(12) United States Patent
Khandare et al.

(10) Patent No.: US 11,596,607 B2
(45) Date of Patent: Mar. 7, 2023

(54) POLYMER BASED FORMULATION FOR RELEASE OF DRUGS AND BIOACTIVES AT SPECIFIC GIT SITES

(71) Applicant: ACTORIUS INNOVATIONS AND RESEARCH PVT. LTD., Mumbai (IN)

(72) Inventors: Jayant Jagannath Khandare, Pune (IN); Abhijit Gothoskar, Pune (IN); Nilesh Kulkarni, Aurangabad (IN); Gourishankar Aland, Pune (IN); Shashwat Banerjee, Kalyan (IN); Rituja Gupta, Sindhudurg (IN)

(73) Assignee: ACTORIOUS INNOVATIONS AND RESEARCH PVT. LTD., Mumbai (IN)

( * ) Notice: Subject to any disclaimer, the term of this patent is extended or adjusted under 35 U.S.C. 154(b) by 0 days.

(21) Appl. No.: 16/605,652

(22) PCT Filed: Apr. 10, 2018

(86) PCT No.: PCT/IB2018/052496
§ 371 (c)(1),
(2) Date: Oct. 16, 2019

(87) PCT Pub. No.: WO2018/193337
PCT Pub. Date: Oct. 25, 2018

(65) Prior Publication Data
US 2020/0129442 A1 Apr. 30, 2020

(30) Foreign Application Priority Data
Apr. 18, 2017 (IN) .............. 201721013710

(51) Int. Cl.
*A61K 9/48* (2006.01)
*A61K 9/00* (2006.01)

(52) U.S. Cl.
CPC .......... *A61K 9/4816* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 4,738,817 A * | 4/1988 | Wittwer | B29C 66/14 264/328.14 |
| 4,871,549 A | 10/1989 | Ueda et al. | |
| 5,171,580 A | 12/1992 | Iamartino et al. | |
| 5,451,411 A * | 9/1995 | Gombotz | A61K 38/204 424/499 |
| 5,482,718 A | 1/1996 | Shah et al. | |
| 6,039,975 A | 3/2000 | Shah et al. | |
| 6,228,396 B1 | 5/2001 | Watts | |
| 9,693,981 B2 * | 7/2017 | Masri | A61P 25/32 |
| 9,884,024 B2 * | 2/2018 | Joshi | A61K 9/48 |
| 2013/0078308 A1 | 3/2013 | Hashimoto et al. | |
| 2017/0042820 A1 | 2/2017 | Lebo et al. | |

FOREIGN PATENT DOCUMENTS

| | | |
|---|---|---|
| WO | 2005030173 A1 | 4/2005 |
| WO | 2011045775 A1 | 4/2011 |
| WO | 2018193337 A2 | 10/2018 |

OTHER PUBLICATIONS

Florence and Siepmann, "Time controlled drug delivery systems", Modern Pharmaceutics, vol. 2: Applications and Advances, Informa Healthcare, USA Inc. 2009, pp. 1-22.

Garbacz, G., et al., Dissolution of mesalazine modified release tablets under standard and bio-relevant test conditions, Journal of Pharmacy and Pharmacology, 2014, 1-10.

International Search Report and Written Opinion dated Nov. 15, 2018, for International Application No. PCT/IB2018/52496 (International Filing Date: Apr. 10, 2018).

Kozuch et al., "Treatment of inflammatory bowel disease: a review of medical therapy," World J Gastroenterol, 2008, 14(3), pp. 354-377.

Maroni et al., "Film coatings for oral colon delivery," International Journal of Pharmaceutics, vol. 457, Issue 2, Dec. 5, 2013, pp. 372-394.

Shull et al., "Targeted disruption of the mouse transforming growth factor-beta 1 gene results in multifocal inflammatory disease," Nature, 1992; 359(6397), pp. 693-699.

Talaei et al., "Overcoming therapeutic obstacles in inflammatory bowel diseases: a comprehensive review on novel drug delivery strategies," Eur J Pharm Sci., 2013, 49(4) pp. 712-722.

Youan, "Chronopharmaceutical drug delivery systems: Hurdles, hype or hope?" Adv Drug Deliv Rev., 2010, 62(9-10) pp. 898-903.

* cited by examiner

*Primary Examiner* — Celeste A Roney
(74) *Attorney, Agent, or Firm* — Bryan D. Zerhusen; Nicholas R. Herrel; Cantor Colburn LLP

(57) ABSTRACT

The present invention is related to polymer based formulation for release of drugs and bioactives at gastrointestinal tract specific sites including stomach, intestine and colon.

6 Claims, 3 Drawing Sheets

POLYMER BASED FORMULATION FOR RELEASE OF DRUGS AND BIOACTIVES AT SPECIFIC GIT SITES

CROSS REFERENCE TO RELATED APPLICATIONS

This application is a National Stage Application of PCT/IB2018/052496, filed 10 Apr. 2018, titled POLYMER BASED FORMULATION FOR RELEASE OF DRUGS AND BIOACTIVES AT SPECIFIC GIT SITES, published as International Patent Application Publication No. WO 2018/193337 A2, which claims the benefit and priority to Indian Complete Application 201721013710 filed on Apr. 18, 2017 and incorporated herein by reference in their entirety for all purposes.

FIELD OF INVENTION

The present invention provides desired drug/bio-active release formulation in solid dosage form comprising variable physico-chemical properties of Active Pharmaceutical Ingredients (APIs) and other bio-actives including proteins by means of polymer capsule as a unit dosage form. The above said dosage form comprises natural polymer example, sodium alginate with bi- and/or trivalent ions chemically balanced cations to control the release of drug/bio-actives at specific time and at specific GIT sites.

BACKGROUND OF THE INVENTION

Solid dosage forms and such drug delivery systems with oral route, remains the most desired and accepted route of administration. Oral dosage systems are able to release the drug at a constant rate for a given time period with multiple release profile/s are thus of interest. Conventional solid dosage forms consist of active agent and biologically inert auxiliary substances which are the pharmaceutical excipients. Conventional dosage forms release the drug following which drug is very rapidly dissolved and quickly builds up to a maximum high concentration in GIT. The result is an undulating concentration of the drug in the stomach or intestine, thus in the systemic circulation and tissues. The dosage form may thus release high of or low concentrations of drugs which may under-serve the patient's needs. Often, this may cause problems in maintaining therapeutic drug levels over only brief duration of time which may either lead to an insufficient efficacy provoking an excessive drug dumping. Therefore, for the successful pharmaco-treatment, an ideal drug delivery system should be (a) able to deliver the drug at a rate to co-relate in vivo bioequivalence, and (b) deliver the drug to its targeted site, for example, as in the case of inflammatory bowel disease (IBD), irritable bowel syndrome (IBS) and colonic cancer. The conventional pharmaceutical formulation strategies do not meet these delivery abilities required by specific conditions or diseases.

Various controlled drug delivery systems (CDDS) have been developed with aspects of time and spatial control of drug release. CDDS are conventionally achieved by following approaches, i) diffusion controlled, ii) degradation or erosion controlled, iii) osmotic controlled and iv) swelling controlled. This results with constant uniform concentration of drug in blood and tissues over a period of time, with the following advantages: (i) reduced amount of drug administered reduces the problems of side effects, improving the safety of therapy, (ii) the patient compliance is achieved with such types of dosage forms, as the frequency of administration is considerably lower.

In CDDS, the dosage form has uniform packing characteristics over a range of different particle size distributions and is capable of processing into various solid dosage forms viz. tablets, capsules, pellets, enteric coating, etc. Conclusively, rate of drug release is controlled by the rate of water penetration into the dosage form matrix. In order to achieve the desired drug release profile, various rate controlling polymers are added into the dosage form. This increases the process and thus the cost of the therapy. However, the drug dumping is associated especially with such unit dosage forms. Further, various specialized technologies such as, osmotic controlled release formulations require number of processing operations which subsequently increases the processing time. Multiple processing of unit dosage form includes coating with specific polymers, e.g. enteric coating (Time controlled drug delivery systems, In: A. T. Florence, J. Siepmann (Eds.) Modern Pharmaceutics Volume 2: Applications and Advances, Informa Healthcare USA; Inc., New York, N.Y.; 2009; 1-22).

Newer solid dosage forms are envisioned to achieve the drug and other actives to be released at various GIT sites. However, all solid dosage forms overrides the physiological implications, including the gastric pH, varied gastric retention times and other physiological limitations including the organ emptying time. For example, many drugs (e.g. Omeprazole, esomeprazole, pantoprazole, etc.) are unstable in stomach pH thereby results in drug degradation and hydrolysis, ineffective drug absorption and lowered therapeutic efficacy. This is overcome by process technology now routinely practiced as a 'pelletization process' followed by enteric coating using pH sensitive polymers (example, Eudragit).

While, circadian rhythms are of great significance in therapeutics such in selecting the specific time of drug administration which directly influences its pharmacokinetics, adverse effects, efficacy and overall therapeutic outcome. Chronopharmaceutics provides drug release that ideally matches the circadian rhythm (24 hour) of the body in association with a specific disease, for e.g. hypertension (U.S. Pat. No. 6,229,396).

The chronopharmaceutical technologies based on physical and/or chemical activation for controlled drug release that is intended for different route of administration (Adv Drug Deliv Rev., 2010, 62, 898-903). Several diseases, wherein the symptoms are most intense during night time or early morning, for example, cardiovascular diseases, bronchial asthma, duodenal ulcer, osteoarthritis, etc. are shown to follow circadian rhythms. Thus, providing treatment at the required hour would mean a more logical and clinically relevant approach to development of oral pulsatile drug delivery systems. Currently, there are major roadblocks for the successful transition of such system to reach technology to patient. These include the challenges to identify adequate (i) Suitable polymers, (ii) rhythm engineering modeling and their system biology and (iii) regulatory guidance.

On the other hand, pulsatile drug delivery systems have gained increasing interest during recent years because of its ability to release the drug rapidly and completely after a defined lag time. Pulsatile release profiles are suitable for drugs with (1) higher first-pass metabolism, (2) which develop biological tolerance, (3) which are targeted to a specific site in GIT, such as colon, (4) which need protection from degradation, and to meet the chronotherapeutical diseases. Ambulatory blood pressure has reported to exhibit diurnal pattern with a surge in the early morning time which is considered to be a major factor behind high risk of cardiac death, ischemic and hemorrhagic stroke. Therefore, there is a need of an antihypertensive drug to have higher plasma concentration for morning surge in blood pressure[9, 10, 11].

Furthermore, various formulation strategies to target the colon include the polymeric coatings of the dosage form to provide the delayed drug release because of the degradation of coating facilitated by presence of either change in pH, pressure, time-dependent polymeric films or microorganism flora.

Colon targeted drug delivery system need to overcome the hurdles in the form of acidic pH of stomach and slightly alkaline pH in small intestine. They are expected to initiate drug release in large intestine. These systems work on the principle of solubilization of polymer coating at alkaline pH above 7. Polymers such as Eudragit L100 which is soluble above pH 5.5 to 6.5 and Eudragit S100, soluble above pH 7 are commonly used.

The wide variety of enzymes, such as glucoronidase, xylosidase, arabinosidase, amylase, pectinase, xylanase, galactomannanase, nitroreductase, azoreductase, deaminase, urea dehydroxylase have been reported to produce microbiota of colon. Polysaccharides of natural origin obtained from plant, algal, animal or microbial origin such as calcium pectinate, chitosan, chondroitin sulphate, galactomanan, and amylose are mostly used for micro-biota-activated coatings.

There are few issues from the viewpoint of regulatory bodies associated with azo-compounds such as firstly, the need for an organic solvent for their solubilization and secondly non-established safety profile. In general, to achieve drug delivery to colon typically comprises solid dosage forms coated with pH resistant polymers. Colon targeting is achieved by using biodegradable polymers such as cellulose acetate pthalate and shellac. On the other hand, enteric coating is achieved by using various acrylic polymers.

Pressure-dependent devices are meant to be ruptured because of the relatively elevated pressure in large intestine compared to small intestine due to peristaltic movement. Finally, time-dependent coatings releases the pay load in colon as a consequence of either of the following mechanisms, which are, timed erosion, disintegration or enhanced permeability irrespective of above mentioned physiological variables. It has been hypothesized that, there is a marked decrease in the pH of proximal large intestine of IBD patients. This could be the cause in few of the instances, that coating of Eudragit S100 has failed to dissolve as intact tablet. On the other hand, as revealed by scintigraphic evaluation, tablets coated with Eudragit L100, were found to dissolve in the distal small intestine (Eur. J. Pharm. Sci., 2013, 49, 712-722; Int. J. Pharm, 2013, 457, 372-395).

U.S. Pat. No. 6,228,396 discloses a colonic drug delivery composition comprising a starch capsule containing drug. Colon targeting is achieved by means of a coating comprising of a pH sensitive material, a redox sensitive material or a material which could be broken down by the enzymes or microbiota present in the colon. Capsule formulations containing API mesalamine for colon targeting is available in market (e.g. Delzicol, Apriso, Pentasa). Similarly, tablet formulations coated with a pH dependent coating which dissolves above pH 7 are also available in market (e.g. Asacol HD, Lialda).

Commercially, there are various solid dosage forms with widespread therapeutics for oral administration, for example, Delzicol™, Apriso™, Pentasa™. U.S. Pat. Nos. 5,482,718 and 6,039,975 disclose colon-targeted delivery system wherein the core is comprised of a drug and a carrier and the said core is coated with an erodible polymer layer with/without Eudragit®. The use of pH-dependent polymers in combination with acidic/amphoteric drugs such as mesalamine bears several difficulties. The desired drug delivery profile from modified release formulations containing ionisable drugs and/or ionic polymers such as enteric coating can be affected by pH and composition on intestinal fluids (Journal of Pharmacy and Pharmacology; 2014; 1-10). U.S. Pat. Nos. 5,171,580, 6,039,975, WO2011045775, WO 2005030173 and U.S. Pat. No. 4,871,549 disclose coated drugs maximizing the use of excipients in the formulation leading to increase in the number of manufacturing processes.

In general, in order to achieve CDDS, the technologies involve tableting process and the use of coating of solid dosage forms with different polymers. Essentially, the pharmaceutical process involves multi-steps and use of multiple excipients. And yet the 'tunability' to achieve the control over the drug release profiles is questionable with often drug dumping and lower patient compliance.

In the present invention, Applicants propose a non-tableting, non-coating platform (capsule as a solid dosage form) using natural polymer's to control the release of drug/bioactives at specific time and at various specific GIT sites. The rate of release of actives is achieved as immediate-, extended-, sustained, lag-, pulsatile-, or delayed-drug release profiles (e.g. site—colon delivery). Herein, capsules as a dosage form comprising sodium alginate with bi- and/or trivalent chemically balanced ions to control the release of drug/bio-actives at specific time and at specific GIT sites are demonstrated.

SUMMARY OF THE INVENTION

The present invention provides solid dosage formulation in the form of capsule to achieve multiple drug dissolution profiles. The dosage form protects degradation of the drug in gastric environment (APIs e.g. Omeprazole, esomeprazole, pantoprazole and all grouped azoles), or achieve controlled/extended release of drug/bio-actives, and attain lag or pulse release profile (e.g. Metoprolol, Amlodipine, etc.). The dosage form also achieves the delayed release in small or large intestine or at colon site (e.g. Mesalamine, budesonide, infliximab, peptides, proteins or other bioactives etc.). The preparation of such solid dosage formulation is also provided. The invention also encompasses that such modified drug dissolution platform is useful to supplement the nutraceuticals or dietary minerals with divalent cations (e.g. $Na^+$, $Mg^{++}$, $Ca^{++}$).

The present invention relates to a drug delivery formulation in the form of polymer capsules for delivering different drugs and bioactives at various GIT sites, including stomach, intestine and colon having varied drug release profiles.

The capsule of the present invention achieves the delayed release of the anti-inflammatory or anticancer drugs, e.g. mesalamine, 5-flurouracil, etc. for colon delivery.

The formulation composition reported in the present invention does not involve application of coating step by using any of the available enteric or biodegradable polymers nor any other excipient.

The present invention comprises the dosage form using polymer of natural origin, sodium alginate which is resistant to acidic pH. The thickness and toughness of the polymer/s is so adjusted that, it remains intact during its transit through stomach and intestine. Once the capsule reaches colon, it will achieve the burst release of the drug because of the swelling of polymer at higher pH values and also by subsequent rapid erosion. The release profiles achieved are highly essential in treating Crohn's disease, colon cancer, Irritable Bowl Syndrome (IBS) and other GI-related disorders.

One aspect of the invention is to design the capsules using alginate crossed linked with multi-cations in the form of Form-Fill-Seal (FFS) process for site-specific delivery as colon targeting.

DETAILED DESCRIPTION

Figure 1:
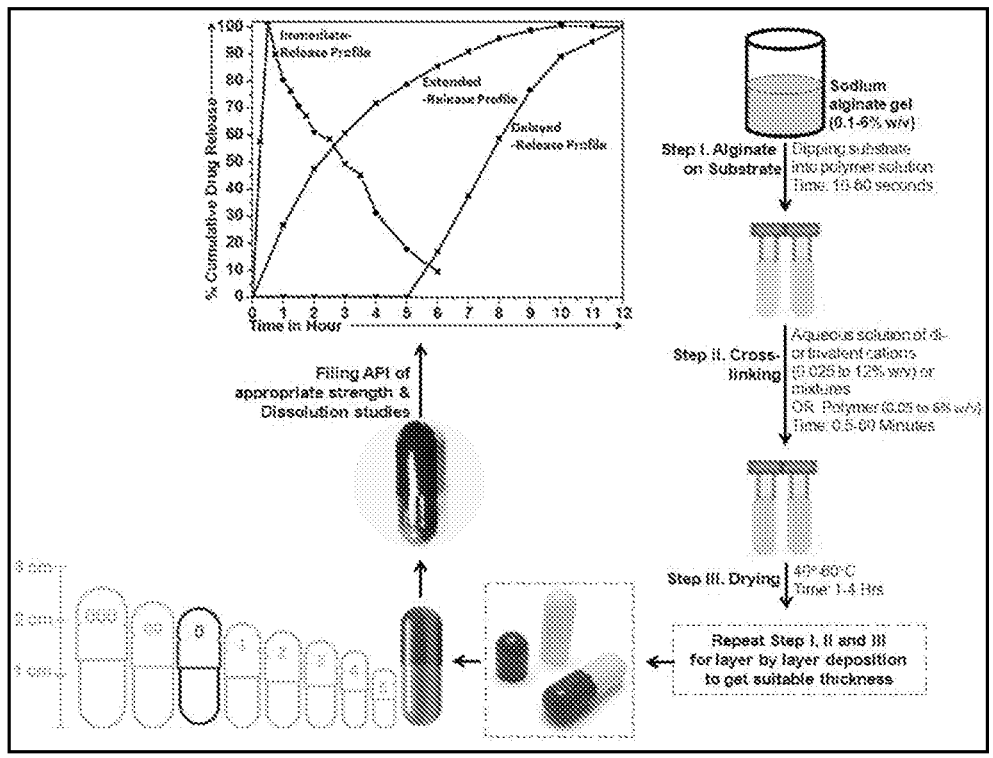
FIG. 1. Schematic for preparation of capsule dosage form comprising polymer and ions and the Dimensions of drug releasing polymer capsule using multi ions of alginate gel.

The present invention is related to a polymer based formulation for release of drugs and bio-actives at GIT specific sites. In one embodiment, the invention describes a dosage form comprising sodium alginate with bi- and/or trivalent chemically balanced cations to control the release of drug/bio-actives at specific time and at specific GIT sites. Herein, the applicant details a modified drug releasing pharmaceutical formulation as a capsule dosage form comprising Form-Fill-Seal (FFS) capsule processing. This brings ease of administration, subsequently avoiding inconvenient route of administration for dosage forms like suppositories and enemas. Avoidance of systemic absorption of drugs and consequently its unwanted distribution to tissues in the body is also achieved. This is applicable for site specific drug targeting for efficient local treatment of large bowel diseases, such as inflammatory bowel disease, ulcerative colitis, amebiasis, and colonic cancer. The polymeric capsule can deliver drugs or proteins and peptide drugs. Rectal administration is also limited by availability of lesser number of dosage forms (solutions, foams, enemas, and suppositories) and drug also remains localized to rectum and distal colon if administered by this route.

In another embodiment, the invention describes the preparation of said formulation and its release profile for wide-ranging therapeutics as a "capsule" prepared by finely-tuned composition of bi- and/or trivalent cations and natural and/or synthetic polymer/s or combination thereof to control the release of drug/bioactives at specific time and at specific GIT sites.

The term "modified release" includes, but is not limited to, immediate-, extended-, sustained-, lag- and pulsatile-, or delayed-, or combination of drug release profiles in pharmaceutical formulation.

The present invention demonstrates a novel composition that offers greater multiplicity and flexibility in the release profile to be obtained with finely tuned natural polymer, sodium alginate using di- and/or tri-valent cations and natural/semi-synthetic/synthetic polymer. The relative ionic affinity and ability to form gels has been extensively studied for natural polymer, sodium alginate and a range of divalent cations is established the following series for the concentration of divalent cations required to bring about gelation of alginate: Ba<Pb<Cu<Sr<Cd<Ca<Zn<Ni<Co<Mn, Fe<Mg.

The mechanical properties of alginate gels are dependent mainly upon and affinity towards bivalent or trivalent cations which bring about (a) stiffness of the individual polymer chains in alginate and (b) the nature and the strength of the forces whereby bi- or trivalent metal ions bind different chains together. Thus, alginate gels are crosslinked with bi- or trivalent cations.

In the present invention, the release rate profiles of bioactives is achieved when the alginate concentration was varied from 1% to 6% w/v ionic concentrations. For example, when alginate concentration was higher than 2%, it promoted the saturation for ionic binding. Also, addition of $Fe^{+++}$ promoted faster diffusion of $Ca^{++}$ and reduced $Ca^{++}$ equilibrium concentration. Also, $Fe^{+++}$ ions entrapped in the alginate capsule promoted greater absorption of water compared to pure alginate gel.

Further, by addition of $Mg^{++}$ ions, the alginate achieves lower gelation almost 4 times than the equivalent amount of $CaCl_2$ and/or $FeCl_3$.

The formulation of the present invention allows the release of drug/bioactive to reach at specific time and at specific site/s in a controlled manner e.g. extended-, sustained-, lag-, pulsatile-, or delayed-drug release profiles. The formulation is modulated by process of forming capsule shell to achieve desired release profile/s. Herein, the type and content of natural polymer blended and/or cross-linked with bi- and/or trivalent ions in the form of their salts with one or many natural or synthetic excipients/polymers to reach appropriate thickness of the layer on substrate was considered.

It is observed that for oral administration of controlled-, sustained-, pulsatile-, extended- or delayed-release pharmaceutical compositions comprising bare API (No API processing), capsule shell composition provide a high unit dose of the active ingredient; exhibit desired in-vitro release profiles and in-vivo performance. Moreover, the formulation of the invention presents the advantage that it is cost effective since one polymer with bare API is needed to control the release of the active ingredient, thus facilitating relatively cheaper manufacturing process. In addition to optimum dissolution profile, the formulation of the invention presents an advantage of compatibility between natural polymer and drug/bioactive with better stability on storage.

Capsule shell composition comprises sodium alginate, bi- and/ or trivalent cations in the form of their salts, for example: $CaCl_2$, $FeCl_3$, $BaCl_2$, $MgCl_2$, and $MnCl_2$ and/ or polymers, for example: CMC, HPMC, HPC, starch, cross-linked sodium CMC/HPC; high-molecular weight polyvinylalcohols; gums such as natural gum, psyllium husk, tamarind gum, agar, agrose, sodium alginate, carrageenan, gum arabic, gum ghatti, gum karaya, gum tragacanth and xanthan gum; hydrophilic colloids such as alginates, carbopol and polyacrylamides; other substances such as arbinogalactan, pectin, amylopectin, gelatin, and N-vinyl lactams; polysaccharides; chitosan, hyaluronic acid and the like. Combinations of any two or more of these cations, and/or polymers having the required properties to achieve specific drug release profiles are within the scope of the invention.

The dosage form of the present invention is a capsule comprising (a) drug/bioactives including peptide, proteins, natural/mineral oils, enzymes, vitamins and mixtures thereof; (b) polymer sodium alginate blended with natural or synthetic polymers. The polymer blends that can be used with cross-linked alginate includes but not limited to HPMC, CMC, PVA, gelatin, starch and so on.

In one embodiment, the present invention comprises pharmaceutical composition of capsule shell comprising:
(a) 0.01 to 6% w/v aqueous solution of Sodium alginate.
(b) 0.025 to 18% w/v of bi- and/or trivalent ions in the form of their salts,
(c) 0.01 to 10% w/v natural and/or semi-synthetic and/or synthetic polymer/s.

In another embodiment, the pharmaceutical composition of the present invention comprise a therapeutically effective quantity of drug/bioactive or its pharmaceutically acceptable salts. The said composition is in a solid unit dosage form, as a capsule, made up of a single polymer of natural origin, which can be tuned to achieve various drug release profiles, such as, immediate (e.g. metformin capsule, FIG. 4), pulsatile (e.g. metoprolol hydrochloride capsule, FIG. 5) and colon targeted or delayed release (e.g. mesalamine capsule, FIG. 6).

The pharmaceutical composition of the present invention provides protection from acidic environment in the stomach for proton pump inhibitor drugs without the need to apply enteric coating; these drugs include but not limited to Omeprazole, Rabeprazole, Pantoprazole and so on, which act by immediate drug release as soon as the dosage form reaches proximal part of small intestine. Thus the pharmaceutical composition of the present invention can deliver site specific drug release to colon for various APIs (e.g. mesalamine, budesonide, infliximab, etc.) as well as proteins and peptides, etc.

The pharmaceutical composition of the present invention can also be prepared using any of the substrates such as stainless steel capsule pins, glass rods, teflon rods and brass capsule pins. It is envisaged that the pharmaceutical composition of the present invention which is a capsule formulation can be altered by achieving suitable thickness and toughness so as to deliver drug to the colonic region. The required thickness and toughness of the composition is achieved by increasing the number of capsule layers which may vary from one to eight. Thus the drug release can be modified or defined by the number of layers of the substrate. As the number of alginate layers increases, the release rate of bioactive from the capsule decreases.

Furthermore, the pharmaceutical composition of the invention is delivered via systemic route when the drug/bioactive is a protein or a peptide.

The pharmaceutical composition of the invention is useful for delivering the drug/bioactive at specific site and specific time in conditions such as IBD and cancer. Thus, the bioactive release rate can be tuned by changing the number of layers of capsules.

Due to high ionic crosslinked system and H+ resistant alginate polymer capsule, the rate of hydration in stomach until its emptying time will be negligible. This will preserve the release of bioactive. Further, due to high ions the capsule will have lower hydration in intestinal buffers. The capsule at intestinal pH and due to long retention time there will initiate hydration resulting in swelling. While, it reaches to colon, the swelled capsule is expected to release the bioactive in colon pH. This can be tuned based on number of alginate layers and crosslinking ratio's of ions.

Furthermore, the formulation of the invention delivers the bioactives by oral route when the drug/bioactive is protein or a peptide. It is expected that the capsule will protect these bioactives from early release in stomach and intestine. The rate of release will be delayed when the capsule reaches colon.

EXAMPLES

The pharmaceutical composition of the present invention describes the dosage form comprising sodium alginate crosslinked with bi- and/or trivalent ions to control the release of drug/bio-actives at specific time and at specific GIT sites.

Example 1

Suitable grade of alginate polymer was selected and a gel was prepared in distilled water in concentration ranging from 0.1-6% w/v. A substrate (e.g. stainless steel capsule pins, glass rods, teflon rods and brass capsule pins), was dipped into the alginate polymer gel for a time period of 10-60 seconds and removed. In the next stage, the substrate on which polymer gel was coated was dipped into aqueous solution of di- or trivalent ions or their mixtures (example, $CaCl_2$, $FeCl_3$ and $MgCl_2$ having concentration from 0.025 to 12% w/v) thereof in the form of their salts and/or polymer having concentration from 0.05 to 6% w/v and 0.01 to 6% w/v respectively for a time period between 30 seconds to 1 hour (FIG. 1). This process allows cross-linking which leads to solidification of alginate. The substrate was then removed and dried in hot air oven at any temperature between 40° C. to 60° C. for time period of 1-4 hours.

To get suitable thickness, layer by layer depositions from 1 to 8 layers of the polymer was achieved by repeating the same steps mentioned above (FIG. 1). Suitable thicknesses of the capsules allow generating different drug release profiles. Later on, the substrates containing dried polymer layers were again dipped into same concentration of salt/s as used in the initial stage of polymer cross-linking, which allows complete hydration and formed capsules were then removed with ease from the substrate.

Example 2

Figure 2:
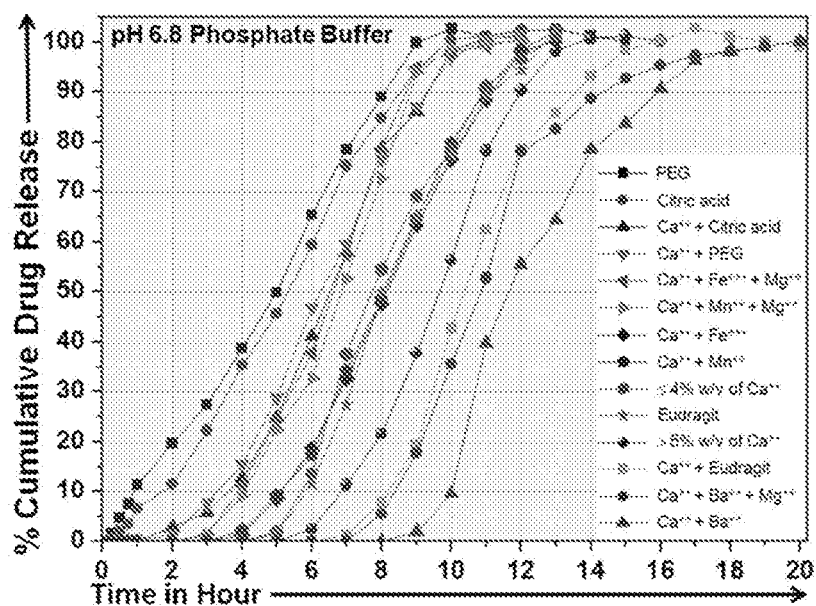
FIG. 2. Varied release profiles of APIs with alginate and/or bi- or trivalent ions and/or polymers.

Drugs or bio-actives are filled into alginate capsules prepared by method as mentioned in Example 1. The capsules were cross-linked with either polymeric blend/s or bi-/trivalent cations in the form of their salt/s and/or combinations thereof to achieve delivery. As the solubility of the drug changes the rate of release kinetics was altered. The cross-linking of cations with alginate showed varied release profiles ranging from immediate to delayed release up to 8 hours (FIG. 2). Therefore, cross-linked alginate capsules are prepared to obtain wide-ranging release profiles, to improve the bioavailability or stability and to target drug to specific sites. This also offers the advantages, like limiting drug fluctuation within therapeutic range, reducing the side effects, and decreasing dose frequency and improving patient compliance.

Example 3

Capsules were allowed to dry and filled up with suitable API and subjected to in vitro drug/bio-active dissolution study. The characterization of final empty capsules was carried out by measuring the following physical specifications:
Empty Capsule weight (mg)
Empty Capsule weight of cap and body (mg)

Empty Capsule-body volume capacity (ml)
Empty Capsule weight capacity by formulation density (mg)
Empty Capsule length (mm)
Empty Capsule individual length/s of cap and body (mm)
Empty Capsule external and internal diameter cap and body (mm)

Physical Characteristic of the Capsule is Provided in Table 1

Physical characterization of final empty capsules

| Entry | Parameter | Size Range |
|---|---|---|
| 1. | Empty Capsule weight (mg) | 170-180 |
| 2. | Empty Capsule weight of cap (mg) And | 66-2 |
|    | Empty Capsule weight of body (mg) | 102-112 |
| 3. | Empty Capsule—body volume capacity (ml) | 0.65-7 |
| 4. | Empty Capsule weight capacity by formulation density (mg) | 250-350 |
| 5. | Empty Capsule length (mm) | 21.2-22.2 |
| 6. | Empty Capsule individual length of cap (mm) | 10.5-11.5 |
|    | Empty Capsule individual length of body (mm) | 18.2-19.2 |
| 7. | Empty Capsule external diameter of cap (mm) | 7.4-7.8 |
|    | Empty Capsule internal diameter of cap (mm) | 7.2-7.6 |
|    | Empty Capsule external diameter body (mm) | 7.0-7.2 |
|    | Empty Capsule internal diameter body (mm) | 6.8-7.0 |

Example 4

Dissolution profile of the following drug compounds were determined using alginate gel and its capsule and it was crosslinked with calcium chloride ions.

Figure 3:
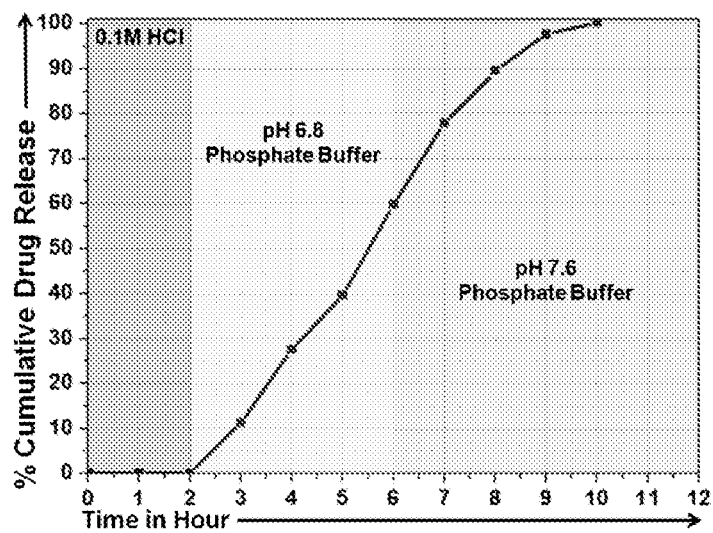
FIG. 3. Dissolution profile of $H^+$ proton pump inhibitor Omeprazole—a pH unstable API.

In FIG. 3, dissolution profile of $H^+$ proton pump inhibitor—Omeprazole as bare API was filled in alginate capsule. Omeprazole was protected from contact with acidic gastric acid in stomach until its relevance gastric empting time for more than 2 hours. This was achieved by designing>03 layered alginate capsules which are cross-linked with cations in the form of their salt such as $Ca^{++}$.

Figure 4:
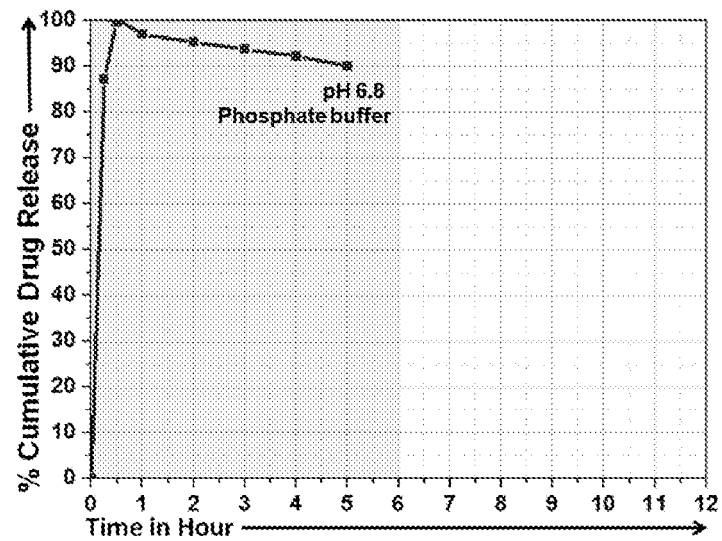
FIG. 4. Dissolution profile of Metformin Hydrochloride showing Immediate Release (IR) Profile.

FIG. 4 shows the dissolution profile of Metformin hydrochloride in alginate capsule. 02 layers of alginate capsules were prepared and cross-linked with cations in the form of their salt/s such as $Ca^{++}$. The dissolution profile indicated that ≥90% drug release happened within an hour for water-soluble drug was achieved. The said pharmaceutical composition is an immediate release dosage form, characterized by its dissolution profile wherein after 30 minutes at least 85% by weight of the active ingredient/s is dissolved.

Figure 5:
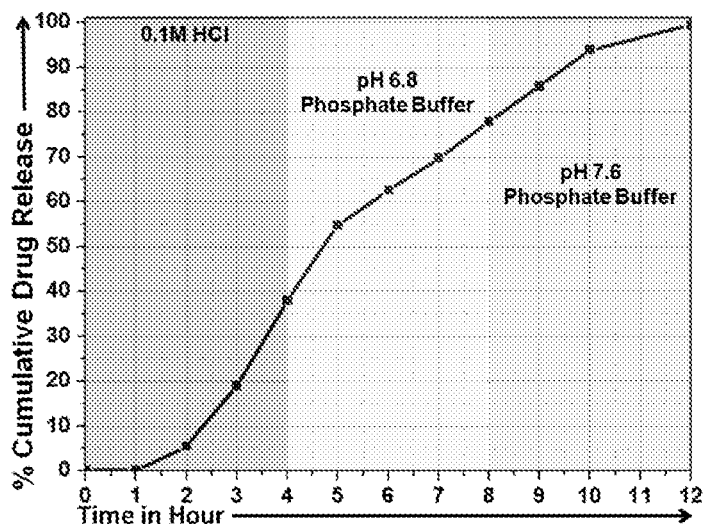
FIG. 5. Dissolution profile of Metoprolol tartrate in 0.1M HCl (4 Hrs), pH 6.8 Phosphate buffer (4 Hrs) and pH 7.6 Phosphate buffer (4 Hrs).

FIG. 5 shows the dissolution profile for alginate capsule having Metoprolol tartrate in 0.1M HCl (4 Hrs), pH 6.8 Phosphate buffer (4 Hrs.) and pH 6.8 phosphate buffer (4 Hrs). The results indicate that a pulsatile release with chronopharmacological behavior. This was achieved by 03 layers of alginate which was cross-linked with bivalent cations in the form of their salt/s such as $Ca^{++}$. The pulsatile release of Metoprolol tartrate with an hour of lag period influence drug release that ideally matches the circadian rhythm (24 hour) of the body in association with a specific disease.

Figure 6:
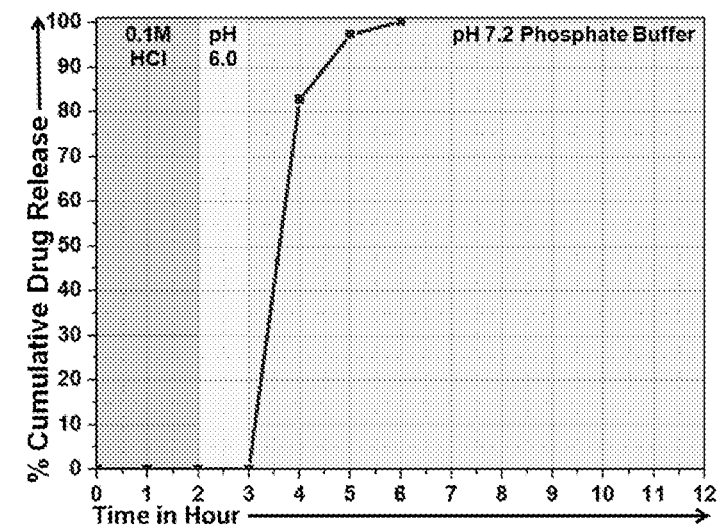
FIG. 6. Dissolution profile of Mesalamine in 0.1M HCl (2 Hrs), pH 6.0 Phosphate buffer (1 Hr) and pH 7.2 Phosphate buffer (3 Hrs).

FIG. 6 shows dissolution profile for alginate capsule having Mesalamine in 0.1M HCl (2 Hrs), pH 6.0 phosphate buffer (1 Hr) and pH 7.2 Phosphate buffer (3 hrs). The results indicate colon targeted modified release. This was achieved by 03 layers of alginate cross-linked with bivalent cations in the form of their salt/s such as $Ca^{++}$. The delayed release of Mesalamine with 0≥3 hour of lag period influence drug to reach preferred sites of delivery-distal gut (ileum and/or colon) without absorption from the small intestine ability at distal sites in the gut and its release in colon that increases the residence time to treat Ulcerative colitis and IBD. With altering the number of the alginate capsule, modified-profiles releases were achieved from immediate-release viz. metformin hydrochloride to a drug with a delay after its administration (delayed-release dosage) or for a prolonged period of time (extended-release [ER, XR, XL] dosage) or to a specific GIT target viz. colon (targeted-release dosage).

We claim:

1. A polymer capsule for delivery of an active pharmaceutical ingredient (API) consisting of:
    a shell formed of a plurality of layers from a dried solution of from 0.01 to 10% w/v of at least one polymer selected from HPMC, CMC, PVA, starch or a combination thereof, and from 2-6% w/v of sodium alginate cross-linked with from 0.025 to 18% w/v of bivalent ions, trivalent ions or a combination thereof, the remainder with water,
    wherein the capsule contains the API inside the capsule, and wherein the capsule prevents release of the API in the acid environment of the stomach.

2. The polymer capsule of claim 1, wherein the polymer capsule is delivered as immediate drug release, extended-drug release, sustained-drug release, lag-drug release, pulsatile-drug release, delayed-drug release, modified drug release, or any combinations of profiles at a specific time and site.

3. The polymer capsule of claim 2, wherein the API is formulated into a form selected from the group consisting of powder, pellets, enteric-coated granules, and tablets.

4. The polymer capsule of claim 1, wherein the API is selected from a group consisting of water-soluble, water-insoluble, acid-labile, non-acid labile, proteins and peptides.

5. The polymer capsule of claim 1, wherein the said polymer is cross-linked with bi- and/or trivalent ions in the form of their salts.

6. A method of treating irritable bowel disease or cancer, the method comprising providing the polymer capsule of claim 1, including a therapeutically effective amount of an API for treating irritable bowel disease or cancer disposed therein, and administering the API-containing polymer capsule to a patient in need thereof, wherein the API is delivered to the colon and is effective for the treatment of irritable bowel disease or cancer.

\* \* \* \* \*